(12) United States Patent
Kusminsky

(10) Patent No.: US 8,540,639 B2
(45) Date of Patent: Sep. 24, 2013

(54) ULTRASONOGRAPHIC IDENTIFICATION OF A SENTINEL LYMPH NODE

(76) Inventor: Roberto Kusminsky, Charleston, WV (US)

( * ) Notice: Subject to any disclaimer, the term of this patent is extended or adjusted under 35 U.S.C. 154(b) by 187 days.

(21) Appl. No.: 12/766,420

(22) Filed: Apr. 23, 2010

(65) Prior Publication Data

US 2010/0274135 A1    Oct. 28, 2010

Related U.S. Application Data

(60) Provisional application No. 61/172,096, filed on Apr. 23, 2009.

(51) Int. Cl.
*A61B 8/14* (2006.01)
*A61K 49/22* (2006.01)

(52) U.S. Cl.
USPC ............................................. 600/458; 424/9.1

(58) Field of Classification Search
USPC ........................................................ 600/458
See application file for complete search history.

(56) References Cited

U.S. PATENT DOCUMENTS

| | | | |
|---|---|---|---|
| 5,611,344 A | 3/1997 | Bernstein et al. | |
| 5,707,607 A | 1/1998 | Quay | |
| 6,205,352 B1 | 3/2001 | Carroll | |
| 6,444,192 B1 * | 9/2002 | Mattrey | 424/9.52 |
| 2003/0232084 A1 * | 12/2003 | Groman et al. | 424/486 |

FOREIGN PATENT DOCUMENTS

WO  WO 2007034196  * 3/2007

OTHER PUBLICATIONS

Goldberg et al., Sentinel Lymph Nodes in a Swine Model with Melanoma: Contrast-enhanced Lymphatic US, Radiology vol. 230 No. 3, pp. 727-734, Mar. 2004.*
Williamson et al., Polymer Contrast Particles for Cellular Imaging With Ultrasound and MRI, IEEE Ultrasonics Symposium, pp. 648-651, 2007.*
Fang Yang et al., "Superparamagnetic nanoparticle-inclusion microbubbles for ultrasound contrast agents," Physics in Medicine and Biology, vol. 53, pp. 6129-6141, 2008.
Tatsuo Inoue et al., "Differential diagnosis of nodular lesions in cirrhotic liver by post-vascular phase contrast-enhanced US with Levovist: comparison with superparamagnetic iron oxide magnetic resonance images," Journal of Gastroenterology, vol. 40, pp. 1139-1147, 2005.
Stephen J. Norton and Tuan Vo-Dinh, "Imaging the distribution of magnetic nanoparticles with ultrasound," IEEE Transactions on Medical Imaging, vol. 26, No. 5, pp. 660-665, 2007.
Eddy C. Hsueh and Armando E. Giuliano, "Sentinel lymph node technique for staging of breast cancer," The Oncologist, vol. 3, pp. 165-170, 1998.

* cited by examiner

*Primary Examiner* — Tse Chen
*Assistant Examiner* — Patricia Park
(74) *Attorney, Agent, or Firm* — Spilman Thomas & Battle, PLLC

(57) ABSTRACT

A method of detecting at least one axillary sentinel lymph node using ultrasonography is described. The method comprises injecting an iron hydroxide compound into a patient at or near a suspected tumor site in the breast and waiting an amount of time required for the iron hydroxide compound to enter cells of the sentinel lymph node. The axillary area near the injection site may then be analyzed using ultrasonography to identify at least one sentinel lymph node. Once identified, a small sample of tissue from the identified sentinel lymph node may be taken for pathological analysis to aid in determination of the stage or extent of breast cancer.

18 Claims, 2 Drawing Sheets

ULTRASONOGRAPHIC IDENTIFICATION OF A SENTINEL LYMPH NODE

CROSS-REFERENCE TO RELATED APPLICATIONS

The present application claims the benefit of prior provisional application Ser. No. 61/172,096, filed Apr. 23, 2009, the contents of which provisional application is hereby incorporated herein by reference.

STATEMENT REGARDING FEDERALLY SPONSORED RESEARCH

Not Applicable

THE NAMES OF THE PARTIES TO A JOINT RESEARCH AGREEMENT

Not Applicable

INCORPORATION-BY-REFERENCE OF MATERIAL ON DISC

Not Applicable

BACKGROUND

1. Technical Field of the Invention

This invention pertains generally to the identification of sentinel lymph nodes using ultrasonography and, more particularly, to the use of an iron sucrate solution with ultrasonography to identify sentinel lymph nodes.

2. Background of the Invention

The treatment of breast cancer often requires a direct surgical approach to the tumor within the breast and to the lymph nodes underneath the arm (axilla). The axillary nodes are an important predictor of disease outcome and the information derived from their pathological analysis determines therapeutic alternatives. Those nodes are positive for neoplastic cells in as many as 40% of breast cancers. In the past, the typical approach was to remove as many possible axillary nodes in conjunction with the breast tumor. A morbidity rate of about 20% was associated with this practice. Thus, several methods were developed to identify and biopsy the sentinel lymph node.

The lymph ducts of the breast drain to one lymph node first, the sentinel node, before draining through the rest of the lymph nodes in the axilla. The cellular elements that drain to the lymph or that gain access to lymph nodes are typically the circulating white cells or phagocytes that are involved in the cellular defense mechanism. Although these cells are very large (several tens of micrometers in diameter), they gain access to the lymph space by their ability to deform and migrate through tiny openings. These cells patrol the extracellular space, phagocytose materials, and carry such materials into the lymph and the lymph nodes for further action by the immune system. When cancer occurs in tissues or organs, its loose matrix allows the dislodging of cells that gain access to the lymph space. However, because they lack the functionality of white blood cells, they can become trapped in the lymph node and grow. The first node that traps the cancer is called the sentinel lymph node.

Limiting dissection to the sentinel lymph node can therefore predict the status of the remainder of the nodal system. When the sentinel lymph node is free of neoplastic tumor cells, the remainder of the nodes are negative in nearly 100% of the cases. When the node is found to contain neoplastic cells, it is the only positive node in over 60% of cases and contains five times more micrometastasis than nonsentinel nodes (Hsuch & Giuliano, *The Oncologist* 1998; 3:165-170). So, in addition to staging, sentinel node resection provides some therapeutic benefit, as all micrometastases are removed in a majority of cases.

Thus, if the sentinel lymph node is free of neoplastic tumor cells, further lymph node biopsies and (further) lymph node dissections can be avoided. The standard of care today allows the surgeon to select patients for axillary dissection only when deemed necessary, a decision based on the information derived from analysis of the sentinel lymph node. In other words, a sentinel lymph node without tumor cells allows the patient to avoid an axillary dissection and the associated morbidity.

Sentinel lymph nodes have been identified by injecting a marking agent into the tumor-bearing tissue and tracing the pathway of the marking agent through the lymphatic system. Visible marking agents such as dyes have been employed to visually detect the sentinel lymph node with the naked eye. Such a method requires significant surgical dissection. Furthermore, the nodes are indistinguishable from the surrounding tissue unless darkly stained and the dyes unfortunately have an unpredictable and rapid clearance rate.

Currently, the sentinel lymph node is routinely identified indirectly, by targeting the signal produced by a radioactive tracer isotope which has been incorporated, for example by phagocytosis, by cells within the lymph node. The radioactive gamma emission signal is picked up with a signal detector (a "gamma probe"). The surgeon then makes an incision in the appropriate location and removes the sentinel lymph node, which is analyzed by the pathologist while the patient is still under anesthesia. If the exam reveals that the sentinel lymph node does have cancer cells, the surgeon proceeds with an axillary dissection at that time. Otherwise, the patient is sent home and awaits the result of the permanent pathologic analysis, which may show cancer cells not seen at the time of surgery. When this is the case, the patient must be returned to the operating room to undergo an axillary dissection. An additional disadvantage of this procedure is that both the patient and medical personnel are exposed to potentially harmful doses of ionizing radiation. Radioactive isotopes also pose environmental contamination and disposal issues.

Attempts have been made to examine the axilla with ultrasonography, a non-invasive imaging technique. While it is sometimes possible to visualize lymph nodes, there is currently no method to clearly identify the sentinel lymph node. If this were possible, a simple needle biopsy could determine if the patient requires further or no additional surgery.

Thus, while the current standard of care for patients diagnosed with breast cancer includes identification of the sentinel lymph node at the time of surgery, it is still accomplished using both a radioactive tracer substance, such as a gamma ray emitting isotope, and a vital blue dye, such as Isosulfan Blue (Lymphazurin).

The present invention replaces both the radioactive tracer isotope and the vital blue dye with an iron-containing compound, which surprisingly allows positive recognition of the sentinel lymph node by ultrasonographic exam. The procedure of the present invention involves identification of the sentinel lymph node with ultrasonographic equipment using a non-isotopic compound. Once located, the sentinel lymph node may be evaluated for the presence of tumor cells using standard pathologic analysis. There are dramatic advantages to the patient under these circumstances: patients will not receive radioactive material, no general anesthesia or sedation will be needed, incisions might not be necessary, the identification would be done by visualization (in contrast with the currently indirect identification method), and the opportunity to obtain this information prior to the final surgical procedure could avoid the need for the patient to undergo further surgery in certain situations.

SUMMARY

A first embodiment of the present invention is directed to a method of detecting at least one sentinel lymph node, comprising: injecting an iron compound into a patient; waiting an amount of time; analyzing an area in which the at least one sentinel lymph node is suspected to exist using ultrasonography; and identifying the at least one sentinel lymph node. This method may further comprise the step of removing a small sample of tissue from the identified sentinel lymph node for pathological analysis, wherein the pathological analysis is used to determine the presence or extent of a disease.

In an embodiment, the disease may be breast cancer, and the at least one sentinel lymph node may be an axillary lymph node in a breast in which breast cancer is suspected to exist. Thus, the injection may be made in a subareolar location or in close proximity to the areola.

In an embodiment, the iron compound may be an iron hydroxide-sucrose complex, such as, for example, Venofer®.

In an embodiment, the amount of time is the time required for the iron compound to enter cells of the at least one sentinel lymph node, which may be, for example, a time of about fifteen minutes.

In an embodiment, identifying the at least one sentinel lymph node includes analyzing, by ultrasonography, a lymph and looking for a region of the lymph that appears brighter than the surrounding tissue, or is of higher contrast when compared to the surrounding tissue.

Another embodiment of the present invention is directed to a method of detecting at least one axillary sentinel lymph node in a breast cancer patient, comprising: injecting an iron hydroxide compound into a patient; waiting an amount of time required for the iron hydroxide compound to enter cells of the at least one axillary sentinel lymph node; using ultrasonography to analyze an area in which the at least one axillary sentinel lymph node is suspected to exist; and identifying the at least one axillary sentinel lymph node. This method may further include the step of removing a small sample of tissue from the identified axillary sentinel lymph node for pathological analysis, wherein the pathological analysis is used to determine the stage or extent of breast cancer.

Yet another embodiment of the present invention is directed to a sonographic scanner to be directed toward a patient in which an iron compound has been infused to locate a sentinel lymph node.

Another embodiment of the present invention is directed to a system for detecting at least one sentinel lymph node. That system includes an iron compound to be injected into a patient and allowed to enter cells of at least one sentinel lymph node and an ultrasonographic device to analyze an area in which the at least one sentinel lymph node is suspected to exist to identify the at least one sentinel lymph node.

BRIEF DESCRIPTION OF THE DRAWINGS

Aspects, features, benefits and advantages of the embodiments herein will be apparent with regard to the following description, appended claims, and accompanying drawings, where:

DETAILED DESCRIPTION

Figure 1:
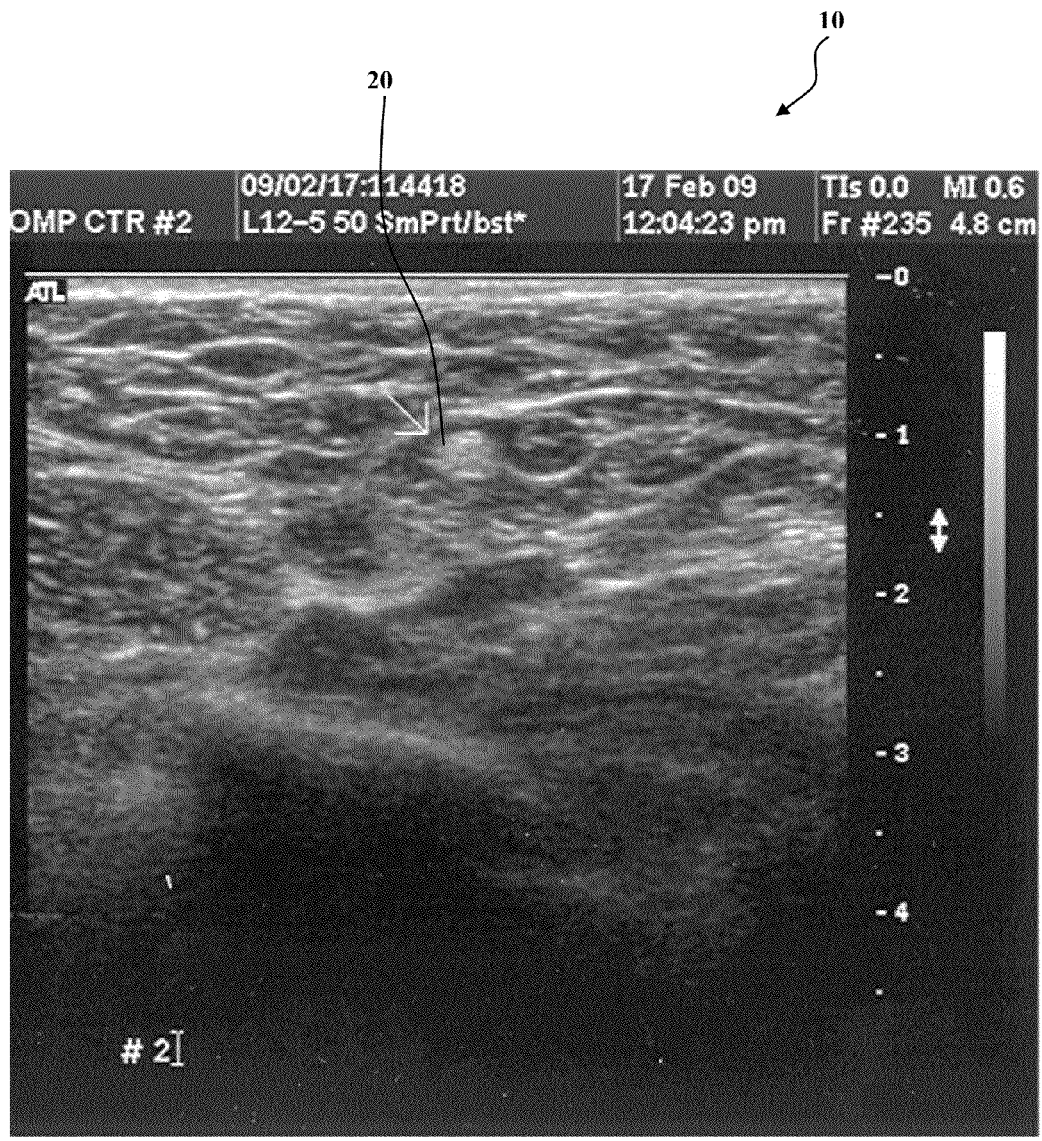
FIG. 1 is an exemplary ultrasonographic image illustrating a sentinel lymph node that has been identified using methods of the present invention.

In the following description, the present invention is set forth in the context of various alternative embodiments and implementations involving methods by which sentinel lymph nodes may be identified using ultrasonography and, more particularly, to the use of iron-containing solutions with ultrasonography to identify sentinel lymph nodes. The ultrasonography may be accomplished using ultrasonographic equipment, which may include, in various embodiments, a sonographic scanner, an ultrasonic imaging system, or any equipment used to create a sonogram. It will be appreciated that these embodiments and implementations are illustrative and various aspects of the invention may have applicability beyond the specifically described contexts. Furthermore, it is to be understood that these embodiments and implementations are not limited to the particular compositions, methodologies, or protocols described, as these may vary. The terminology used in the following description is for the purpose of illustrating the particular versions or embodiments only, and is not intended to limit their scope in the present disclosure which will be limited only by the appended claims.

Throughout the specification, reference to "one embodiment," "an embodiment," or "some embodiments" means that a particular described feature, structure, or characteristic is included in at least one embodiment. Thus appearances of the phrases "in one embodiment," "in an embodiment," or "in some embodiments" in various places throughout this specification are not necessarily all referring to the same embodiment. Those skilled in the art will recognize that the various embodiments can be practiced without one or more of the specific details or with other methods, components, materials, etc. In other instances, well-known structures, materials, or operations are not shown or not described in detail to avoid obscuring aspects of the embodiments.

"Optional" or "optionally" means that the subsequently described event or circumstance may or may not occur, and that the description includes instances where the event occurs and instances where it does not. In addition, the word "comprising" as used herein means "including, but not limited to". Throughout the specification of the application, various terms are used such as "primary", "secondary", "first", "second", and the like. These terms are words of convenience in order to distinguish between different elements, and such terms are not intended to be limiting as to how the different elements may be used.

It must also be noted that as used herein and in the appended claims, the singular forms "a", "an", and "the" include the plural reference unless the context clearly dictates otherwise. Thus, for example, reference to a "node" is a reference to one or more nodes and equivalents thereof known to those skilled in the art, and so forth. Unless defined otherwise, all technical and scientific terms used herein have the same meanings as commonly understood by one of ordinary skill in the art.

This invention provides methods for identification of at least one sentinel node by ultrasonographic exam using an iron-containing compound that will allow recognition of the sentinel node via ultrasound imaging. In various embodiments, the present invention provides potential advantages to the patient over the prior art, including one or more of at least the following:
1) No radioactive material is used;
2) The procedure does not require the complexities of operating room access;
3) No incision is required;
4) Neither general anesthesia nor sedation are needed;
5) No special equipment is needed;
6) The expense of the procedure as is currently performed is reduced;
7) If the node is positive for the presence of tumor cells, one extra surgical procedure could potentially be avoided; and
8) Therapeutic decisions can be made more readily.

Successful visualization of the sentinel node with ultrasound may use a substance that behaves in a manner similar to that of currently-used radioactive tracer isotopes and vital dyes. Such a substance may be first incorporated into cells of the lymph nodes, such as by a process of phagocytosis. Using such a substance may ease the process of ultrasound recognition by targeting at least one sentinel lymph node, causing that node to be easily visualized by the ultrasonic waves. Such a process may include using iron particles in accordance with the present invention, as described herein. A current source of such iron particles is the iron sucrate solution Venofer®, an iron sucrose injection used to replenish iron stores in patients with iron deficiency. This dietary iron (III) hydroxide supplement has been prescribed for approximately 50 years and exhibits a remarkable safety record. Venofer® is a brown, sterile, aqueous complex of polynuclear iron (III)-hydroxide in sucrose. The iron complex has a molecular weight of approximately 34,000-60,000 daltons and a proposed structural formula of $[Na_2Fe_5O_8(OH)3(H_2O)]_n m(C_{12}H_{22}O_{11})$ where n is the degree of iron polymerization and m is the number of sucrose molecules associated with the iron (III) hydroxide.

Venofer® has been demonstrated to be safe for both IV push injection and infusion. The subcutaneous injection of Venofer® also appears to have no ill-effect on the patient. A report describing the spillage of large doses of the medication outside the vein into the subcutaneous tissues producing discoloration demonstrated that the drug does not act as an irritant, and the discoloration of the skin eventually disappeared.

The use of iron hydroxides in accordance with the methods of this invention produces a strong ultrasonographic image. One such image 10 of an iron hydroxide concentrated in a sentinel lymph node 20 can be seen in FIG. 1, in accordance with an embodiment. Iron taken up by the cells of a lymph node becomes concentrated in a lymph node or nodes, thus making it easy to see those structures when examined with ultrasonography. For clarity, the sentinel lymph node 20 is also identified in FIG. 1 with an arrow. A case study using this approach showed no adverse reactions of any type to the skin at the injection site of the Venofer® iron hydroxide-sucrose complex, and provided a successful ultrasonographic demonstration of a sentinel lymph node.

Figure 2:
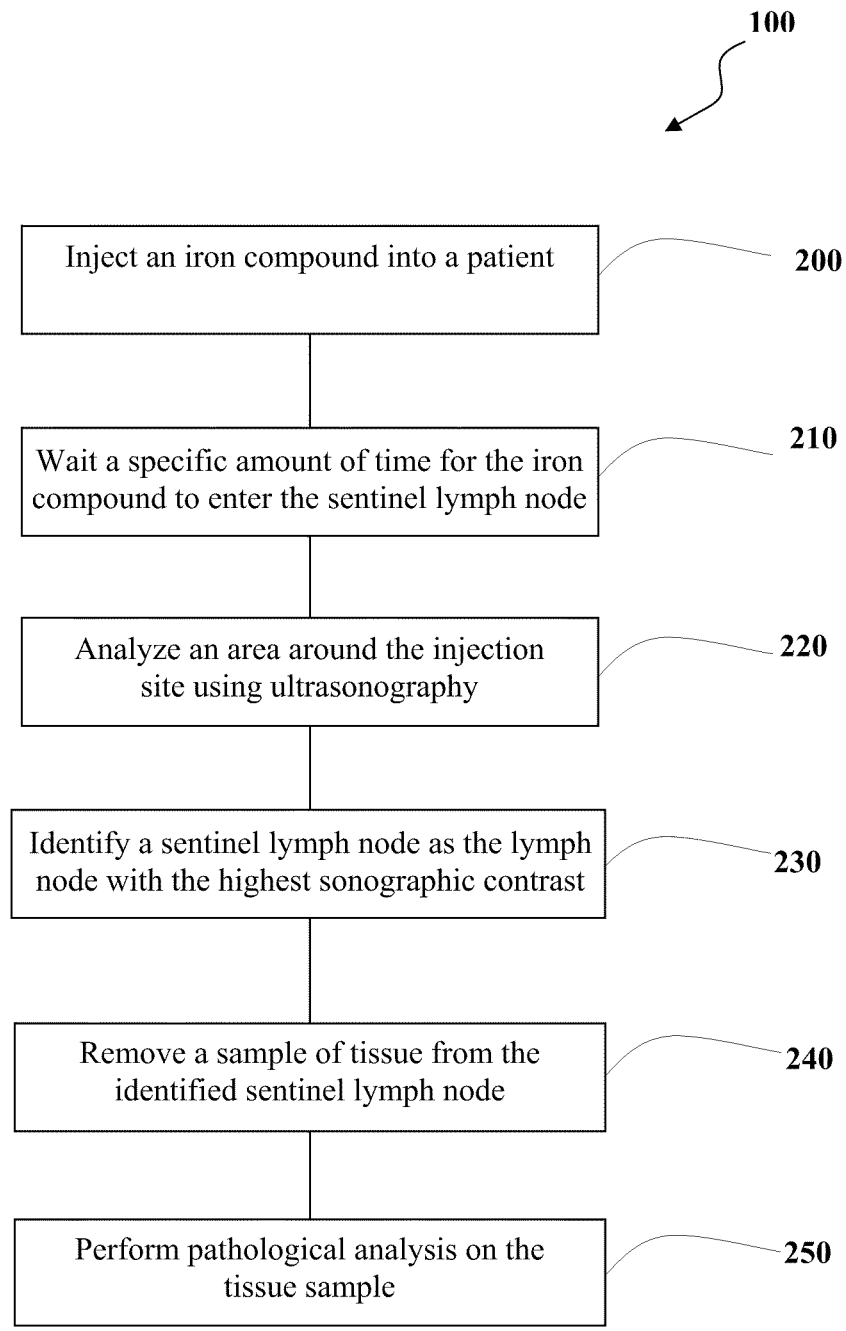
FIG. 2 depicts an exemplary flow diagram of a method for identification of at least one sentinel lymph node using methods of the present invention.

With reference to FIG. 2, an exemplary flow diagram of a method 100 by which sentinel lymph nodes may be identified using ultrasonography is depicted. At 200, an iron-containing compound is injected into a human subject. The injection may be made at any point on the body, but typically such an injection may be at a point near a suspected tumor. The iron-containing compound may be any iron-containing compound, including but not limited to, iron hydroxides such as those used as dietary iron supplements. For example, in one embodiment, the iron-containing compound is Venofer®. At 210, a specific amount of time is allowed to pass, allowing the iron-containing compound to enter cells of the lymph system and target the sentinel lymph node. This time may vary depending upon the injection site. For injection to the axilla in the diagnosis and treatment of breast cancer, the time may be about 15 minutes in an embodiment.

After the aforementioned time has passed, the area near the injection site may be analyzed, at 220, using an ultrasound probe. Any ultrasound equipment may be used. This area may be analyzed to identify, at 230, at least one sentinel lymph node as the lymph node with the highest sonographic contrast (brightest region on the sonogram). At 240, a small sample of tissue may be taken from the identified sentinel lymph node. Such a sample may be excised by needle biopsy, by another minimally invasive technique or by any other desired technique. At 250, the sample may be used for pathological analysis. Such analysis may aid in the identification of abnormal cells and may help to determine the existence and extent of a disease, such as cancer.

Thus, an embodiment of the present invention provides a method of detecting a sentinel lymph node, comprising: injecting an iron compound into a patient; waiting an amount of time; analyzing an area in which the at least one sentinel lymph node is suspected to exist using ultrasonography; and identifying the at least one sentinel lymph node. In an embodiment, the iron compound is an iron hydroxide-sucrose complex, such as, for example, Venofer®. Further, the amount of time waited may be the time required for the iron compound to enter cells of the at least one sentinel lymph node, a time of about fifteen minutes in one embodiment. Identifying the at least one sentinel lymph node may include analyzing lymph using ultrasonography and looking for a region of the lymph that appears brighter than the surrounding tissue.

This method may further comprise the step of removing a small sample of tissue from the identified sentinel lymph node for pathological analysis, wherein the pathological analysis is used to determine the presence or extent of a disease.

Humans have approximately 500-600 lymph nodes distributed throughout the body, with clusters found in the underarms, groin, neck, chest, and abdomen. Diseases in many of these organs can be diagnosed through pathological examination of the local lymph nodes, more specifically the sentinel lymph node. Thus, the methods of the present invention may have applicability to diseases, specifically cancers, of many organs and tissue of the human body.

Using current conventional techniques, lymph nodes have the potential to be visualized with ultrasonography. However, when lymph nodes are visualized using these current practices, there is no way to determine which one of the visible nodes is the sentinel node. Iron oxide microparticles have been tested in a multitude of settings as contrast agents for ultrasonography (Norton & Vo-Dinh, *IEEE Transactions on Medical Imaging* 2007; 26:660-665) of the liver (Inoue et al., *J Gastroenterol* 2005; 40:1139-1147; Yang et al., *Phys. Med. Biol.* 2008; 53:6129-6141). While these attempts have met with limited success, they have only been targeted to the liver. Thus far, there has been no suggestion that iron hydroxide microparticles could be used as described herein to achieve the unique and important results of this invention.

In accordance with embodiments of the present invention and as described in more detail below, Venofer® iron hydroxide-sucrose complex was injected in a human subject in a subareolar location, and fifteen minutes later a lymph node became easily visible when the armpit was examined with ultrasonography, as illustrated by the sonogram of FIG. 1 and indicated by the arrow shown in FIG. 1.

The ability to identify the sentinel node using methods of the present invention changes the current paradigms of breast cancer care completely. Positively identifying at least one sentinel node by ultrasonography in the outpatient setting allows the physician to determine, with ease, the next step in therapy for patients presenting at different stages of the disease. Furthermore, these diagnostic steps are accomplished with a minimally invasive approach, and may thus need no sedation, no radioactive material, no incision, no special new equipment, and less expense if operating room use and hospitalization can be avoided. This information may affect the care of tens of thousands of patients diagnosed with breast cancer every year.

Thus, an embodiment of the present invention is a method of detecting at least one axillary sentinel lymph node in a breast cancer patient, comprising: injecting an iron hydroxide compound into a patient; waiting an amount of time required for the iron hydroxide compound to enter cells of the at least one axillary sentinel lymph node; analyzing an area in which the at least one axillary sentinel lymph node is suspected to exist using ultrasonography; and identifying the at least one axillary sentinel lymph node. This method may further comprise the step of removing a small sample of tissue from the identified axillary sentinel lymph node for pathological analysis, wherein the pathological analysis is used to determine the stage or extent of breast cancer.

EXAMPLES

Feasibility Study

The following example describes a pilot feasibility/observational study, with patients undergoing the traditional and accepted approach to breast cancer surgery. In this manner, patients have the standard indication for a sentinel node biopsy, and undergo the standard procedure to obtain the sentinel node. This standard approach includes injection with a radioactive tracer isotope on the day of surgery. At the point during surgery that the patient would normally receive the vital blue dye injection, as per the current standard protocol, an injection of iron hydroxide-sucrose complex is made instead. The patient next undergoes the standard surgery, but first an attempt is made to identify the sentinel node with ultrasound equipment. If one or more sentinel lymph nodes become visible (e.g. the node has incorporated the iron hydroxide-sucrose complex) under ultrasound, the node or nodes will be removed in the usual manner with ultrasound guidance and will then be checked for radioactivity, as is the case under normal circumstances. This process allows for an unbiased ultrasonographic recognition of the sentinel node confirmed by detection of the radioactive signal from the tracer isotope with a signal detector. The surgery then proceeds in the normal manner.

Injection of the iron hydroxide-sucrose complex may be made after the patient is under anesthesia, as is standard when a vital blue dye is utilized for sentinel node identification. A dose of 10 to 20 milligrams (1 ml=20 mg) is injected subcutaneously/intradermically depending on the patient's weight. The injection may be in a subareolar location or in close proximity to the areola.

Sentinel node identification may be made by ultrasound exam of the axilla on the affected side. The supraclavicular area may be scanned as well. One ultrasound system that may be used, in an embodiment, for purposes of the invention is a Koninklijke Phillips Electronics N.Y. General Ultrasonic Imaging System fitted with appropriate imaging transducers and QLAB quantification software. The use of such an ultrasound device, particularly with such software, may allow for visualization of the iron hydroxide-sucrose complex in the lymph nodes and make it possible to evaluate their relative intensity to help isolate the sentinel lymph node by way of region of interest quantification, as illustrated, for example, in FIG. 1. In an embodiment, it is contemplated that up to about three signal nodes will be identified in this way to improve the likelihood that the key signal node will be located.

If a node is detected under ultrasound, it may be marked by the surgeon with a small gauge spinal needle, and the normal incision may be made to recover the node(s), as is standard when removing the sentinel node using current surgical practices. In an embodiment, it is expected that the node will be stained brown, and this may be recorded.

Once recovered, the node may be examined directly with the ultrasound probe to assess variations of the ultrasound image in different areas of the node.

Next, the radioactive detector (gamma probe) may be used to determine the level of radioactivity, if any, within the node, and the information may be recorded in the standard way. In the future, after the reliability of the present ultrasound identification method is confirmed, there may be no injection of the radiotracer or use of a gamma probe.

The rest of the procedure may proceed in standard manner, and the ultrasonography probe may be used in conjunction with the gamma probe to assess levels of ultrasound signals in other areas of the axilla. These may then be compared with nodes recognized by traditional radioactive isotope tracer activity to establish the reliability of the novel method of the present invention.

Pathologic examination may be carried out in the usual manner.

Data collection related to the procedure may be performed in the operating room. The information collected may include number(s) of nodes recognized with ultrasound, radioactive measurement of nodes recovered with ultrasound, location of nodes recovered, staining of node(s) recovered, and descriptive information. Pathological reports of all nodes recovered may be collected.

Analysis of the data may be performed using standard statistical software, such as SAS 9.1. Basic descriptive statistics may be used. Comparisons of categorical variables may be performed using contingency table analysis with a Chi-square test to determine statistically significant differences. Identification of the sentinel node by ultrasound exam will be compared to the standard of care by examining the percentage of agreement between the two methods. The kappa statistic will be used as a measurement of this agreement. The number of nodes identified by each method will be compared using a t-test (or non-parametric equivalent if not normally distributed). Conventional criteria ($p<0.05$) may be used to identify statistically significant differences. A correlation agreement of 70% or more may be expected in an embodiment.

Breast Cancer Diagnosis

Methods of the present invention may be used in an outpatient setting to aid in the diagnosis and staging of breast cancers. A patient may be injected with an iron hydroxide compound, such as Venofer®, at a site that is subareolar or areolar, depending on the suspected location of the tumor. For example, if a tumor is suspected in the left breast, the injection may be made at a site that is nearest to the tumor (subareolar or areolar) on the left breast. Dosing may be in any therapeutic range acceptable for the specific iron-containing compound used as part of the invention. In the case of Venofer®, a dose of 10 to 20 milligrams may be administered by injection subcutaneously/intradermically depending on the patient's weight.

In an embodiment, about fifteen minutes after injection, the axilla on the side that was injected may be analyzed using ultrasonography. Regions containing the greatest contrast may be analyzed, with those lymph nodes that represent the sentinel lymph nodes appearing as brighter regions or spots as compared to the surrounding tissue. These areas may be sampled using a simple needle biopsy procedure, if desired. Tissue recovered from the needle biopsy may then be used for a pathological analysis to determine the stage or extent of breast cancer and aid in future treatment decisions. The entire procedure may be accomplished in less than 30 minutes and in an outpatient setting.

While specific embodiments of the invention have been described in detail, it should be appreciated by those skilled in the art that various modifications and alternations and applications could be developed in light of the overall teachings of the disclosure. Accordingly, the particular arrangements, systems, apparatuses, and methods disclosed are meant to be illustrative only and not limiting as to the scope of the invention.

What is claimed is:

1. A method of detecting at least one sentinel lymph node, comprising:
    injecting an iron hydroxide-sucrose complex into a patient;
    waiting an amount of time;
    analyzing an area in which the at least one sentinel lymph node is suspected to exist using ultrasonography; and
    identifying the at least one sentinel lymph node by detecting the injected iron hydroxide-sucrose complex in the at least one sentinel lymph node by the ultrasonography.

2. The method of claim 1, further comprising:
    removing a sample of tissue from the identified sentinel lymph node for pathological analysis.

3. The method of claim 1, wherein the iron hydroxide-sucrose complex is a brown, sterile, aqueous complex of polynuclear iron (III)-hydroxide in sucrose.

4. The method of claim 1, wherein the at least one sentinel lymph node is an axillary lymph node in a breast of which breast cancer is suspected to exist.

5. The method of claim 4, wherein the injection is made in a subareolar location.

6. The method of claim 4, wherein the injection is made in close proximity to the areola.

7. The method of claim 1, wherein the amount of time is the time required for the iron hydroxide-sucrose complex to enter cells of the at least one sentinel lymph node.

8. The method of claim 7, wherein the amount of time is about fifteen minutes.

9. The method of claim 1, wherein identifying the at least one sentinel lymph node includes looking for a region of the lymph being analyzed by ultrasonography which appears brighter than the surrounding tissue.

10. The method of claim 2, wherein the pathological analysis is used to determine at least one of presence and extent of a disease.

11. The method of claim 10, wherein the disease is breast cancer.

12. A method of detecting at least one axillary sentinel lymph node in a breast cancer patient, comprising:
    injecting an iron hydroxide-sucrose complex into a patient;
    waiting the iron hydroxide-sucrose complex to enter cells of the at least one axillary sentinel lymph node;
    analyzing an area in which the at least one axillary sentinel lymph node is suspected to exist using ultrasonography; and
    identifying the at least one axillary sentinel lymph node by detecting the injected iron hydroxide-sucrose complex in the at least one axillary sentinel lymph node by the ultrasonography.

13. The method of claim 12, further comprising:
    removing a sample of tissue from the identified axillary sentinel lymph node for pathological analysis.

14. A sonographic scanner configured to be directed toward a patient in which an iron hydroxide-sucrose complex has been infused to locate a sentinel lymph node.

15. The sonographic scanner of claim 14, wherein the sonographic scanner is directed at a portion of the patient in which the sentinel lymph node is suspected to exist.

16. A system for detecting at least one sentinel lymph node, comprising:
    an iron hydroxide-sucrose complex configured to be injected into a patient and allowed to enter cells of at least one sentinel lymph node; and
    an ultrasonographic device configured to an area in which the at least one sentinel lymph node is suspected to exist to identify the at least one sentinel lymph node detecting the injected iron hydroxide-sucrose complex in the at least one sentinel lymph node.

17. The system for detecting at least one sentinel lymph node of claim 16, wherein the iron hydroxide-sucrose complex is an iron compound to be injected into a patient and allowed to enter cells of at least one sentinel lymph node that is an axillary lymph node in a breast of which breast cancer is suspected to exist.

18. The system for detecting at least one sentinel lymph node of claim 16, wherein the sentinel lymph node appears brighter than the surrounding tissue on the ultrasonographic device.

* * * * *